United States Patent [19]

Mayr et al.

[11] Patent Number: 4,816,602
[45] Date of Patent: Mar. 28, 1989

[54] PROCESS FOR THE PRODUCTION OF CYCLOALKANECARBOXYLIC ACIDS

[75] Inventors: Herbert Mayr, Gross-Groenau; Werner Heilmann, Luebeck; Helmut Vorbrueggen, Berlin, all of Fed. Rep. of Germany

[73] Assignee: Kyowa Hakko Kogyo Co., Ltd., Tokyo, Japan

[21] Appl. No.: 57,203

[22] PCT Filed: Sep. 24, 1986

[86] PCT No.: PCT/DE86/00396
§ 371 Date: May 26, 1987
§ 102(e) Date: May 26, 1987

[87] PCT Pub. No.: WO87/02034
PCT Pub. Date: Apr. 9, 1987

[30] Foreign Application Priority Data

Sep. 26, 1985 [DE] Fed. Rep. of Germany ....... 3534613

[51] Int. Cl.⁴ ............................................. C07C 51/00
[52] U.S. Cl. ................................... 562/504; 562/400
[58] Field of Search ............................. 562/400, 504

[56] References Cited

U.S. PATENT DOCUMENTS 3,450,782 6/1969 Connor .............................. 260/666

Primary Examiner—Michael L. Shippen
Attorney, Agent, or Firm—Millen & White

[57] ABSTRACT

Process for the production of cycloalkanecarboxylic acids of general Formula I

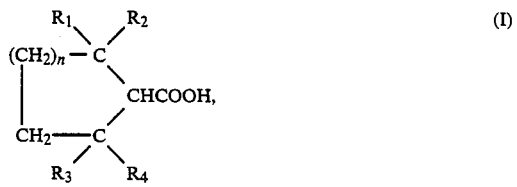

wherein
n means the number 1 or 2,
$R_1$ and $R_3$ are alkyl groups of 1–4 carbon atoms, and
$R_2$ and $R_4$ symbolize hydrogen atoms or alkyl groups of 1–4 carbon atoms, characterized by reacting a compound of general Formula II $$X-CR_1R_2-(CH_2)_n-CH_2-CR_3R_4-X' \quad (II),$$

wherein
n, $R_1$, $R_2$, $R_3$ and $R_4$ have the meanings given above and X and X' mean a hydroxy group, a chlorine atom, a bromine atom, an alkylsulfonyloxy residue, or an arylsulfonyloxy residue,
with 1,1-dichloroethylene;
splitting off hydrogen chloride from the thus-obtained compounds of general Formula III $$X-CR_1R_2-(CH_2)_n-CH_2-CR_3R_4-CH_2-CCl_2X \quad (III),$$

wherein n, X, X', $R_1$, $R_2$, $R_3$ and $R_4$ have the meanings given above; and cyclizing and hydrolyzing, by means of acids, the thus-prepared compounds of general Formula IV $$X-CR_1R_2-(CH_2)_n-CH_2-CR_3R_4-CY=CZX' \quad (IV),$$

wherein
n, X, X', $R_1$, $R_2$, $R_3$ and $R_4$ have the meanings given above, and
Y and Z jointly represent a carbon-to-carbon bond or mean a hydrogen atom and a chlorine atom.

10 Claims, No Drawings

PROCESS FOR THE PRODUCTION OF CYCLOALKANECARBOXYLIC ACIDS

As is known, the cycloalkanecarboxylic acids of general Formula I are valuable intermediate products used, inter alia, for the manufacture of sweeteners (European patent application No. 01 28 654). The production of these compounds according to the known state of the art, however, is very expensive. Compounds of formula I have the general formula

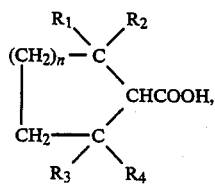 (I)

wherein
n means the number 1 or 2,
$R_1$ and $R_3$ are alkyl groups of 1-4 carbon atoms, and $R_2$ and $R_4$ symbolize hydrogen atoms or alkyl groups of 1-4 carbon atoms.

The process of this invention makes it possible to synthesize these compounds by a substantially simpler route.

The starting compounds for the process of this invention can contain as the alkyl groups $R_1$ through $R_4$, for example, methyl groups, ethyl groups, propyl groups, isopropyl groups, or butyl groups. Based on the commercial exploitability of the products of the process, those starting compounds are preferred wherein the substituents $R_1$ through $R_4$ are identical. Especially preferred starting compounds are those carrying methyl groups as substituents $R_1$ through $R_4$. The starting compounds can carry identical or differing groups as the substituents X and X'. These groups can be polar substituents which can be split off with the formation of carbenium ions. Such substituents are preferably chlorine atoms, bromine atoms, alkylsulfonyloxy groups (such as the methanesulfonyloxy group or the trifluoromethanesulfonyloxy group), or arylsulfonyloxy groups (such as the benzenesulfonyloxy group, the p-bromobenzenesulfonyloxy group, or the p-toluenesulfonyloxy group). These starting compounds can be prepared in a simple way from the corresponding diols by esterification or by exchange of the hydroxy groups for chlorine or bromine. Preferred starting compounds are those carrying as substituents X and X' methanesulfonyloxy groups or, in particular, chlorine atoms or bromine atoms.

In the first stage of the process of this invention, the compounds of general Formula II are reacted under conditions known per se with 1,1-dichloroethylene (see, for example: Angew. Chemie 78: 932 [1966] and 91: 169 [1980]; Tetrahedron Letters 1968, 4979 and 1973, 1569; Chem. Ber. 100: 978 [1967], 103: 3851 [1970] and 106: 2513 [1973]; J. Chem. Soc. Perk. Ed. I, 1973, 2559; Acta Chem. Scand. 34b: 621 [1980]; and Synth. Comm. 14: 113 [1984]; J. Amer. Chem. Soc. 67: 1152 [1945], 68: 1650 [1946], 46: 1655 [1946], and 71: 698 [1949]; as well as J. Org. Chem. 48: 1159 [1983]). Compounds of formula II have the general formula

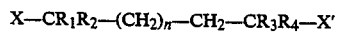 (II), wherein
n, $R_1$, $R_2$, $R_3$ and $R_4$ have the meanings given above and X and X' mean a hydroxy group, a chlorine atom, a bromine atom, an alkylsulfonyloxy group, or an arylsulfonyloxy group. Thus, the compounds of Formula II can be reacted in 1,1-dichloroethylene as the solvent with the addition of strong Lewis acids (such as, for example, iron(III) chloride, iron(III) bromide, tin(IV) chloride, tin(IV) bromide, zirconium(IV) chloride, boron trichloride, boron trifluoride, zinc(II) chloride, gallium(III) chloride or, in particular, aluminum(III) chloride) at a reaction temperature of $-50°$ to $+100°$ C., thus obtaining the compounds of Formula III. Compounds of formula III have the general formula $$X-CR_1R_2-(CH_2)_n-CH_2-CR_3R_4-CH_2-CCl_2X'$$ (III), wherein n, X, X', $R_1$, $R_2$, $R_3$ and $R_4$ have the meanings given above. On the other hand, however, it is also possible to perform this reaction step with the use of other solvents inert under the reaction conditions (for example chlorinated hydrocarbons.

Hydrogen chloride or, if applicable, also HX is split off from the thus-prepared compounds of general Formula III in a second reaction step which can be performed under the conditions likewise described in the above-mentioned publications. For the splitting-off step, aqueous bases, such as sodium hydroxide solution or potassium hydroxide solution, are utilized for economical reasons. It is frequently suitable, for increasing the reaction velocity, to add also phase transfer catalysts (such as, for example, "Aliquat") to the reaction mixture. This reaction step is advantageously conducted at a reaction temperature of 20° to 100° C.

Hydrogen chloride and, if applicable, also HX' can be split off, depending on the type of substituent X and on the reaction conditions, as early as during the first stage of the process of this invention; this is always the case, for example, if X is a free hydroxy group.

In the third stage of the process according to the invention, the compounds of general Formula IV or Formula IV' are cyclized and hydrolyzed by means of acids. Compounds corresponding to the formula IV or IV' have the general formula

 (IV)

and

 (IV')

wherein n, X, X', $R_1$, $R_2$, $R_3$ and $R_4$ have the meanings previously defined. Suitable acids for this reaction step are mineral acids, such as, for example, phosphoric acid, polyphosphoric acid, hydrogen chloride and, in particular, sulfuric acid, organic sulfonic acids, such as methanesulfonic acid or p-toluenesulfonic acid, or strongly acidic carboxylic acids, such as trifluoroacetic acid or especially also formic acid. On the other hand, likewise suitable are, for example, strongly acidic ion exchangers, such as "Amberlite" IR 120 for performing this reaction stage. This reaction step can be performed without the use of additional solvents, in particular in case of using, as the acids, phosphoric acid, polyphosphoric acid, sulfuric acid, or formic acid. On the other hand, however, it is also possible to conduct this reaction in the presence of other solvents, e.g. glacial acetic acid. The reaction temperature utilized for this reaction step depends on the reaction conditions—especially on the acid employed—and is normally about −20° to 120° C.

It is possible by the choice of suitable reaction conditions to perform two or all three stages of the process according to the invention in a one-shot reaction.

The practical examples set forth below serve for rendering a more detailed explanation of the process of this invention.

EXAMPLE 1

(a) Within 15 minutes, 3.75 g of anhydrous aluminum chloride is added to a suspension, cooled to 0° C., of 54.9 g of 2,5-dichloro-2,5-dimethylhexane in 135 ml of 1,1-dichloroethylene. The reaction mixture is stirred for 70 minutes and decomposed by adding 30 g of crushed ice. The organic phase is separated, washed with 2% strength hydrochloric acid, dried over calcium chloride, fractionated under vacuum, and the product, besides unreacted starting material, is 1,1,1,6-tetrachloro-3,3,6-trimethylheptane, bp 67° C. under 0.4 bar.

(b) 1.68 g of 1,1,1,6-tetrachloro-3,3,6-trimethylheptane is combined in 4 ml of dichloromethane with 10 ml of 40% aqueous sodium hydroxide solution and 0.52 g of "Aliquat" 336, and heated under reflux for 17 hours. Then the reaction mixture is allowed to cool, combined with 20 ml of dichloromethane, the organic phase is separated, washed with water, and dried over calcium chloride. The solution is then concentrated under vacuum, yielding 1,6-dichloro-3,3,6-trimethyl-1-heptyne as an oily crude product.

(c) The thus-obtained 1,6-dichloro-3,3,6-trimethyl-1-heptyne crude product is added dropwise within 15 minutes at 0° C. under vigorous agitation to 10 ml of concentrated sulfuric acid. The mixture is then stirred for 14 hours at 0° C., poured on 20 g of ice, and twice extracted with respectively 20 ml of diethyl ether. The organic phase is separated and extracted twice with respectively 20 ml of 10% strength aqueous sodium carbonate solution. The aqueous phase is acidified with concentrated hydrochloric acid, thus obtaining 2,2,5,5-tetramethylcyclopentanecarboxylic acid as a compound which is pure according to NMR spectroscopy and has a melting point of 127°–129° C.

EXAMPLE 2

(a) Under vigorous agitation, 25.2 g of 1,1,1,6-tetrachloro-3,3,6-trimethylheptane is heated to 80° C. with 0.60 g of "Aliquat" (tricaprylmethylammonium chloride) and 50 ml of 40% by weight aqueous sodium hydroxide solution. The mixture is then allowed to cool, diluted with 60 ml of dichloromethane, the organic phase is separated, washed with water, dried with calcium chloride, and the solvent evaporated.

(b) 8.69 g of the crude product 1,6-dichloro-3,3,6-trimethyl-1-heptyne prepared according to Example 2(a) is added dropwise within 30 minutes to 80 ml of boiling, anhydrous formic acid and thereafter is heated for 16 hours under reflux. The mixture is then allowed to cool, 140 ml of water is added, and the mixture is extracted four times with respectively 30 ml of diethyl ether. The combined organic phases are washed with water and subsequently extracted five times by shaking with respectively 20 ml of 10% by weight aqueous sodium carbonate solution. The aqueous phase is acidified with concentrated hydrochloric acid, thus obtaining 2,2,5,5-tetramethylcyclopentanecarboxylic acid as a compound which is pure according to NMR spectroscopy and has a melting point of 127°–129° C.

EXAMPLE 3

(a) At 0° C. under agitation, 3.75 g of aluminum chloride is added in portions within 45 minutes to a thoroughly stirred suspension of 54.9 g of 2,5-dichloro-2,5-dimethylhexane in 135 ml of 1,1-dichloroethylene. The reaction mixture is then stirred for another 100 minutes at 0° C. and combined with 10 ml of water and 20 g of anhydrous calcium chloride. The mixture is then filtered and the excess 1,1-dichloroethylene removed under vacuum. Yield: 88.4 g of a viscous oil from which, by solid-matter distillation, 17.5 g of 2,5-dichloro-2,5-dimethylhexane is recovered. The residue is distilled, thus obtaining 34.3 g of 1,1,1,6-tetrachloro-3,3,6-trimethylheptane as a slightly yellow oil, boiling point 79°–80° C. under 0.5 mbar.

(b) 25.2 g of 1,1,1,6-tetrachloro-3,3,6-trimethylheptane is heated with 0.60 g of tricaprylmethylammonium chloride ("Aliquat" 336) and 50 ml of 40% aqueous sodium hydroxide solution under vigorous agitation to 80° C. for 22 hours. The mixture is then allowed to cool, combined with 60 ml of dichloromethane, the organic phase is separated and dried over calcium chloride. The solvent is thereafter removed under vacuum, and the residue is distilled, thus obtaining 14.7 g of 1,6-dichloro-3,3,6-trimethyl-1-heptyne as a yellow oil, bp 39°–43° C. under 1 mbar.

(c) Under vigorous agitation, 8.29 g of 1,6-dichloro-3,3,6-trimethyl-1-heptyne is added dropwise to 80 ml of 90% strength formic acid, and the mixture is heated for 6 hours under reflux. The mixture is allowed to cool, combined with 300 ml of water, and extracted twice with respectively 50 ml of petroleum ether. The combined organic phases are extracted five times with respectively 30 ml of 10% aqueous sodium carbonate solution. The aqueous phase is acidified with concentrated hydrochloric acid, the precipitated product is recrystallized from petroleum ether, and the product is 4.63 g of 2,2,5,5-tetramethylcyclopentanecarboxylic acid, mp 128°–129° C.

What is claimed is:

1. A process for the production of a cycloalkanecarboxylic acid of general Formula I

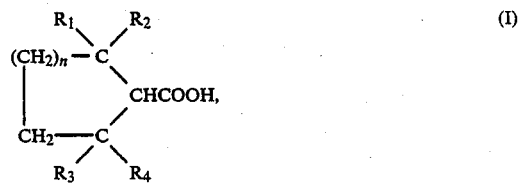

wherein
n is 1 or 2,
$R_1$ and $R_3$ are independently alkyl groups of 1–4 carbon atoms, and
$R_2$ and $R_4$ are independently hydrogen atoms or alkyl groups of 1–4 carbon atoms,
comprising reacting a compound of general Formula II

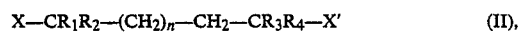

wherein
n, $R_1$, $R_2$, $R_3$ and $R_4$ have the meanings given above and

X and X' are independently a hydroxy group, a chlorine atom, a bromine atom, an alkylsulfonyloxy group, or an arylsulfonyloxy group, with 1,1-dichloroethylene in the presence of a Lewis acid catalyst;

splitting off hydrogen chloride or HX' in the presence of a base from the thus-obtained compound of general Formula III $$X-CR_1R_2-(CH_2)_n-CH_2-CR_3R_4-CH_2-CCl_2X' \qquad (III),$$

wherein n, X, X', $R_1$, $R_2$, $R_3$ and $R_4$ have the meanings given above;

and cyclizing and hydrolyzing, in the presence of an acid, the thus-prepared compound of general Formula IV $$X-CR_1R_2-(CH_2)_n-CH_2-CR_3R_4-C\equiv CX' \qquad (IV),$$

wherein n, X, X', $R_1$, $R_2$, $R_3$ and $R_4$ have the meanings given above, or of the general Formula (IV)'

$$X-CR_1R_2-(CH_2)_n-CH_2-CR_3R_4-C\equiv CCl \qquad (IV)',$$

wherein n, X, $R_1$, $R_2$, $R_3$ and $R_4$ have the meanings given above.

2. A process according to claim 1, wherein $R_1$, $R_2$, $R_3$ and $R_4$ are identical.

3. A process according to claim 2, wherein $R_1$, $R_2$, $R_3$ and $R_4$ are methyl.

4. A process according to claim 1, wherein $R_1$, $R_2$, $R_3$ and $R_4$ are methyl; n is one, and X and X' are Cl.

5. A process according to claim 1, wherein the acid employed in the cyclizing and hydrolyzing step is phosphoric acid, polyphosphoric acid, hydrogen chloride, sulfuric acid, organic sulfonic acid, a strongly acidic carboxylic acid, or a strongly acidic ion exchanger.

6. A process according to claim 5, wherein the sulfonic acid is methane sulfonic acid or p-toluene sulfonic acid.

7. A process according to claim 6, wherein the strongly acidic carboxylic acid is trifluoroacetic acid or formic acid.

8. A process according to claim 7, wherein the acid is formic acid.

9. A process according to claim 1, wherein X and X' are independently a methane sulfonyloxy group, bromine, or chlorine.

10. A process according to claim 1, wherein X and X' are independently bromine or chlorine.

* * * * *